US012636229B2

(12) United States Patent     (10) Patent No.:   US 12,636,229 B2

Jung                    (45) Date of Patent:      May 26, 2026

(54) MANUFACTURING DEVICE FOR GELATIN CAPSULE

(71) Applicant: Soo-Yeong Jung, Siheung-si (KR)

(72) Inventor: Soo-Yeong Jung, Siheung-si (KR)

( * ) Notice: Subject to any disclaimer, the term of this patent is extended or adjusted under 35 U.S.C. 154(b) by 637 days.

(21) Appl. No.: 18/163,912

(22) Filed: Feb. 3, 2023

(65) Prior Publication Data

US 2023/0181423 A1      Jun. 15, 2023

Related U.S. Application Data

(62) Division of application No. 17/085,302, filed on Oct. 30, 2020, now abandoned.

(30) Foreign Application Priority Data

| Jun. 10, 2020 | (KR) | ........................ | 10-2020-0070406 |
| Aug. 5, 2020 | (KR) | ........................ | 10-2020-0098040 |
| Oct. 5, 2020 | (KR) | ........................ | 10-2020-0127963 |

(51) Int. Cl.
    *A61J 3/07*          (2006.01)
    *A61K 9/48*        (2006.01)

(52) U.S. Cl.
    CPC ................. *A61J 3/07* (2013.01); *A61J 3/077* (2013.01); *A61K 9/48* (2013.01)

(58) Field of Classification Search
    None
    See application file for complete search history.

(56) References Cited

U.S. PATENT DOCUMENTS

2020/0054526 A1*   2/2020   Jung  ....................... B41F 17/36

FOREIGN PATENT DOCUMENTS

| JP | 2000084050 | 3/2000 |
| JP | 2005170863 | 6/2005 |
| JP | 2011120619 | 6/2011 |
| JP | 2020503926 | 2/2020 |
| JP | 2020074836 | 5/2020 |
| KR | 101268491 | 6/2013 |
| KR | 20140080844 | 7/2014 |
| KR | 101821587 | 1/2018 |
| KR | 101927148 | 12/2018 |
| KR | 101927151 B1 * | 12/2018 |
| KR | 101951301 | 2/2019 |

OTHER PUBLICATIONS

English translation for KR101927151B1 (2018).*
Japanese Office Action—Japanese Application No. 2020-194022 issued on Nov. 15, 2021, citing JP 2000-084050, JP 2005-170863, JP 2011-120619, JP 2020-074836, and JP 2020-503926.

* cited by examiner

*Primary Examiner* — Sin J Lee
(74) *Attorney, Agent, or Firm* — CANTOR COLBURN LLP

(57) ABSTRACT

Provided is a manufacturing device for a gelatin capsule structured to include a pair of medicinal solution supply units configured to supply medicinal solutions being filled in the capsule while adopting most of structures of an existing manufacturing device for a soft capsule. The device is capable of manufacturing capsules where one capsule is charged with medicinal solutions different from each other, or is capable of increasing productivity compared to the existing manufacturing device.

2 Claims, 3 Drawing Sheets

MANUFACTURING DEVICE FOR GELATIN CAPSULE

BACKGROUND OF THE INVENTION

Field of the Invention

The present disclosure relates generally to a manufacturing device configured to manufacture a soft capsule called a gelatin capsule. More specifically, the present disclosure relates to a manufacturing device for a gelatin capsule in which a pair of medicinal solution supply units configured to supply medicinal solutions being filled into the capsule are provided. In this case, the device may manufacture soft capsules such that medicinal solutions different from each other coexist in one capsule or may supply same medicinal solutions to the capsule through the pair of the medicinal solution supply units, thereby achieving an increase in productivity of the soft capsules compared to existing capsule manufacturing devices.

Description of the Related Art

Soft capsule products used for various purposes are produced using a general method as follows. First, gelatin is heated and liquefied. Next, the liquefied gelatin is spread thinly on a drum of a manufacturing device for a gelatin capsule, turned into a sheet form, and transferred to a manufacturing unit. Subsequently, while being manufactured by a pair of manufacturing rolls, the gelatin capsule is made by being charged with a medicinal solution. This is called a rotary method.

A rotary method manufacturing device includes a sheet manufacturing unit 1 configured to manufacture a thin film-shaped gelatin sheet with a gelatin solution, a capsule manufacturing unit 2 configured to manufacture a capsule with the gelatin sheet, and a medicinal solution supply unit 3 configured to supply a medicinal solution into the gelatin sheet being turned into the capsule.

With reference to FIG. 1, in the sheet manufacturing unit 1, gelatin that has been transformed into a syrup form, that is, a liquid state, in a gelatin tank is supplied to a spreader box B that is connected to a storage tank with a transfer hose. In addition, the gelatin, which is supplied to a relevant spreader box through the transfer hose by being pumped from the storage tank and is in a melted state, is caused to be adjusted in thickness and is applied with the adjusted thickness to an outer circumferential surface of a drum D disposed below the spreader box.

In addition, the gelatin applied to the drum being rotated is cooled to form a sheet and then supplied to the capsule manufacturing unit 2 through a number of transportation rollers.

Next, the capsule manufacturing unit 2 is provided with a pair of manufacturing rolls R that rotate in opposite directions while facing each other in a state that cavities on each of the manufacturing rolls are arranged to correspond to one another at an outer circumference in order to manufacture the outer shell of the soft capsule, wherein each of the cavities is engraved in a shape of one half of the capsule. In addition, a wedge W is mounted on an above side of the manufacturing roll in order to inject the medicinal solution into the cavity and is connected to the medicinal solution supply unit 3 in order to receive the medicinal solution.

More specifically, the wedge W has a distribution plate P coupled thereto, and the transfer lines L configured to supply the medicinal solution are each connected to the nozzles of the medicinal solution supply unit 3 and injection holes formed in the distribution plate. Accordingly, the medicinal solution in the medicinal solution supply unit 3 is supplied to the wedge W by passing through the injection holes in the distribution plate through the transfer lines. That is, the medicinal solution supply unit 3 is composed of one medicinal solution supply unit located at a center of a side behind the capsule manufacturing unit 2, and the medicinal solution is discharged through the transfer lines L from nozzles formed on opposite sides of the medicinal solution supply unit and is supplied to the injection holes formed in the distribution plate.

In summary, two gelatin sheets manufactured in the sheet manufacturing unit 1 are sandwiched between a pair of manufacturing rolls, being rotated, of the capsule manufacturing unit 2. At the same time, a medicinal solution is injected between the gelatin sheets at regular time intervals and is heat-sealed. At the same time, by cutting and manufacturing the gelatin sheet into a capsule shape at the pair of manufacturing rolls, a soft capsule filled with a medicinal solution inside the gelatin film is continuously manufactured.

In addition, as a medicinal solution filled into the gelatin film, not only liquid medicines, but also granular medicines, paste medicines, and the like may be variously considered. With the conventional soft capsule manufacturing device as shown in FIG. 1, only one medicine is input in one capsule, and one capsule is not allowed to be charged with two medicines.

The inventors and applicants of the present disclosure have been developing various related devices in the relevant art and have already proposed a configuration capable of charging one capsule with solid and liquid medicines in Korean Patent No. 10-1268491.

However, the configuration proposed in the Korean Patent No. 10-1268491 has a limitation in that the medicine to be injected is limited to a medicine of a liquid state or a solid state.

In addition, as a way of being able to implement one capsule to be charged with two or more medicines, a medicine manufacturing machine in which a capsule is made of multi-layering films and medicine components are manufactured into the films has been proposed.

Korean Patent No. 10-1927148 and Korean Patent No. 10-1951301 relate to a manufacturing device capable of multi-layering capsule films. However, in the case of such a soft capsule manufacturing device, there is a limitation that additionally required medicine should be added only in a film form.

As such, the applicant of the present disclosure has consistently contemplated a manufacturing device capable of manufacturing soft capsules, in which medicines different from each other are filled in one capsule, and has come up with a manufacturing device for a soft capsule of the present disclosure described below.

In addition, in developing such soft capsule manufacturing devices, a structure that may have an increase in productivity of soft capsules compared to existing manufacturing devices has also been contemplated.

The foregoing is intended merely to aid in the understanding of the background of the present disclosure and is not intended to mean that the present disclosure falls within the purview of the related art that is already known to those skilled in the art.

SUMMARY OF THE INVENTION

Accordingly, the present disclosure has been made keeping in mind the above problems occurring in the related art, and an objective of the present disclosure is to provide a manufacturing device capable of manufacturing soft capsules, in which medicines different from each other are filled in one capsule, without limitation to types of medicines being filled into the capsule.

Alternatively, when the same medicine is input into each of a first space and a second space of one capsule, an objective is to provide a manufacturing device capable of achieving an increase in productivity of soft capsules compared to existing manufacturing devices.

An objective is to provide a manufacturing device for manufacturing a soft capsule capable of achieving a desired purpose by even a simple design change in an existing manufacturing device, rather than developing a manufacturing device with a structure separate from the existing manufacturing device in order to achieve the above objectives.

In order to achieve the above objectives according to the present disclosure, there may be provided a manufacturing device for a gelatin capsule, the device including: a sheet manufacturing unit configured to manufacture a thin film-shaped sheet; a capsule manufacturing unit comprising a pair of manufacturing rolls configured to manufacture a capsule with the sheet manufactured by the sheet manufacturing unit; and medicinal solution supply units configured to supply a medicinal solution to an inside of the sheet being turned into a capsule, wherein the medicinal solution supply units are installed in a pair.

In addition, the medicinal solution supply units may be installed at respective positions behind the pair of the manufacturing rolls, and medicinal solutions being input may be the same medicinal solution.

In addition, the medicinal solution supply units may be installed at respective positions behind the pair of the manufacturing rolls, and medicinal solutions being input may be the medicinal solutions different from each other.

As described above, according to the soft manufacturing device for the gelatin capsule according to the present disclosure, since two medicines different from each other can be easily filled in one capsule without being interfered with by types of medicines being input, capsules can be manufactured so that medicines different from each other are filled in one capsule.

In addition, when the same type of medicines is input, the device has an effect of obtaining twice the capsule production compared to the existing manufacturing device.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Hereinbelow, a manufacturing device for a gelatin capsule according to the present disclosure will be described in detail with reference to the accompanying drawings.

First of all, even though it is expressed as a medicinal solution in the description of the present disclosure, it should be noted that the medicinal solution does not mean only a medicine in a liquid state. That is, in the present disclosure, medicines that may be filled into the capsule are not only the medicines in a liquid state but are various as medicines in a granular state, medicines in a paste state, medicines in a suspension state, and the like.

However, even though the medicines are various types, the various types are commonly referred to as medicinal solutions in the industry. Accordingly, in the following description of the present disclosure, the various types of medicines will be collectively referred to as the medicinal solutions.

Figure 1:
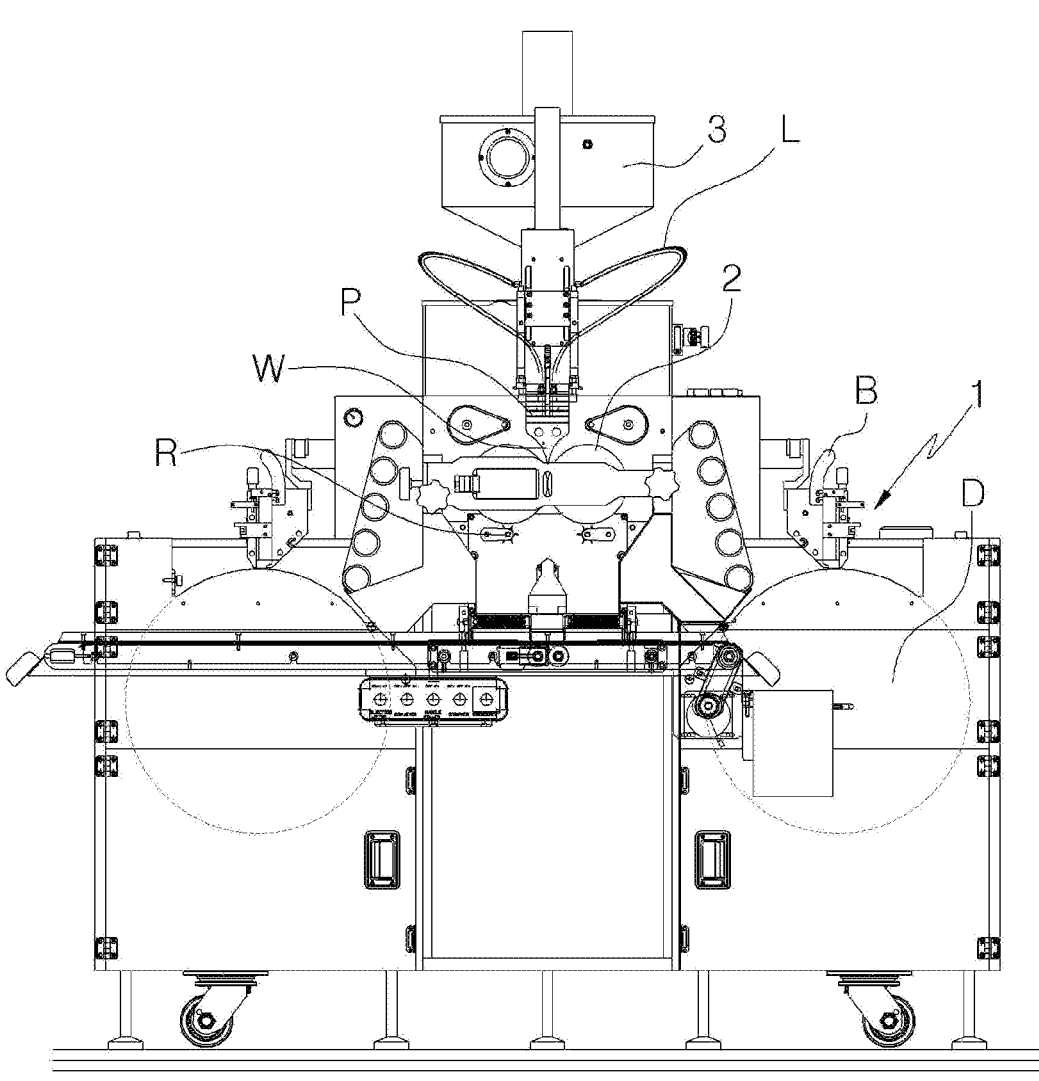
FIG. 1 is a view showing a conventional manufacturing device for a soft capsule.

As mentioned above, FIG. 1 is a view showing a conventional manufacturing device for a soft capsule. When FIG. 2, which is a view schematically showing a manufacturing device for a gelatin capsule according to the present disclosure, is compared with FIG. 1, it is easily confirmed that the present disclosure is changed in the number of installations and locations of the installations of the medicinal solution supply units compared with the conventional manufacturing device for the soft capsule.

That is, in the present disclosure, a pair of the medicinal solution supply units 3 are installed and are each positioned at one side of opposite sides of the left and right of the manufacturing device.

The manufacturing device for the gelatin capsule according to the present disclosure will be described more specifically with reference to FIGS. 2 and 3.

As with the existing device, the manufacturing device for the gelatin capsule according to the present disclosure includes a sheet manufacturing unit configured to manufacture a thin film-shaped sheet, a capsule manufacturing unit configured to manufacture a capsule with the manufactured sheet, and a medicinal solution supply unit configured to supply a medicinal solution into the sheet being turned into a capsule.

In addition, as with the existing device, in the sheet manufacturing unit, gelatin is supplied from a gelatin tank to a spreader box, and the supplied gelatin is in a melted state and comes to adjust a thickness, thereby being applied with the adjusted thickness to an outer circumferential surface of a drum disposed below the spreader box. In addition, the gelatin applied to the drum being rotated is cooled to turn into a sheet and then supplied to the capsule manufacturing unit.

Figure 2:
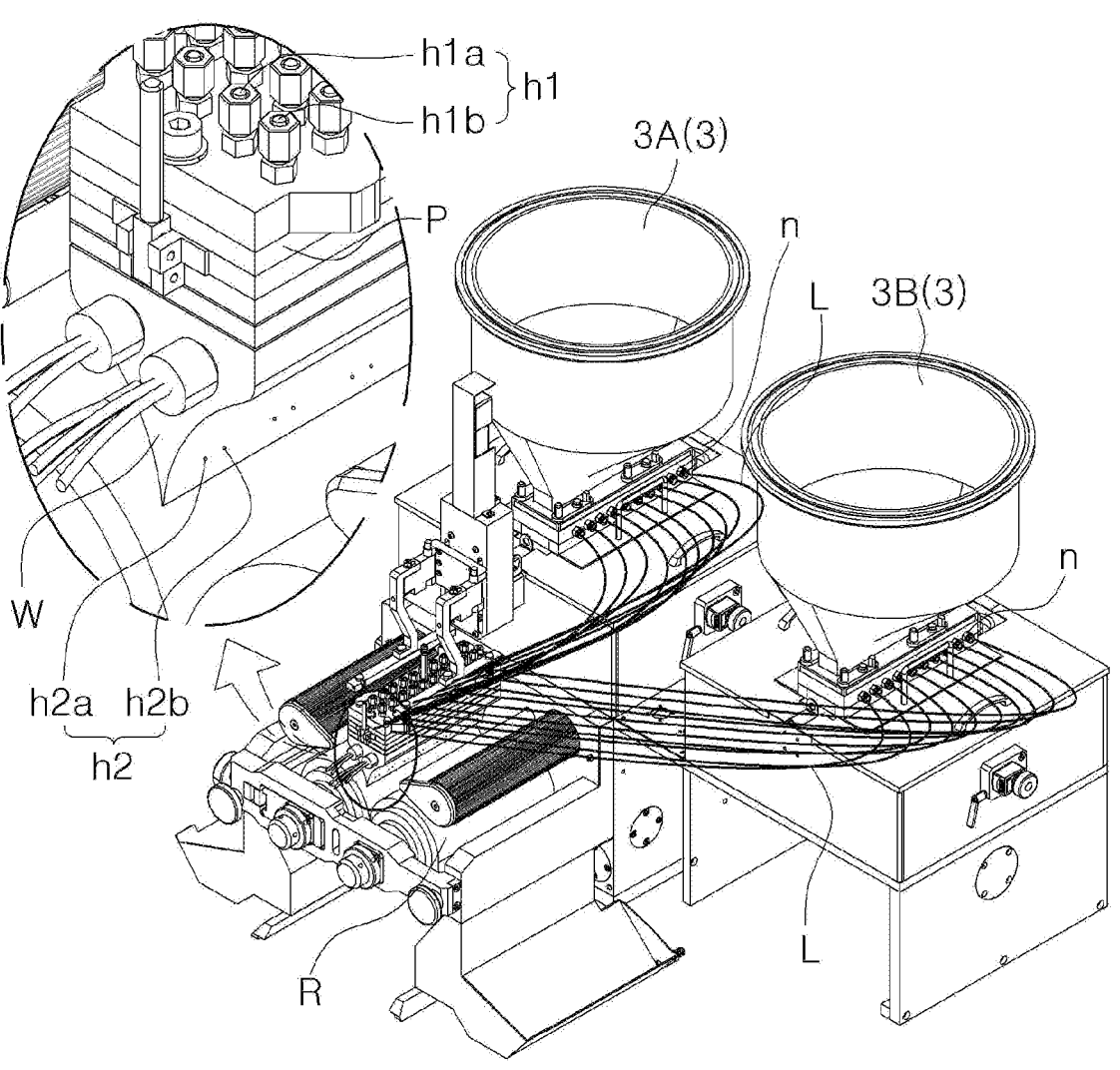
FIG. 2 is a view schematically showing a manufacturing device for a gelatin capsule according to the present disclosure, wherein the view shows a state in which the transfer line is connected only to one side of each of the medicinal solution supply units.

The capsule manufacturing unit includes a pair of manufacturing rolls R on which cavities engraved in a shape of one half of the capsule are arranged (the cavities engraved on the manufacturing roll are not shown in FIG. 2), a wedge W located on an above side of the manufacturing roll and configured to inject a medicinal solution into each cavity, and a distribution plate P installed on a top portion of the wedge.

In addition, the medicinal solution supplied from the medicinal solution supply unit 3 through the distribution plate P and the wedge W is supplied into the sheet being turned into the capsule.

Next, the medicinal solution supply unit 3 is also installed in the present disclosure, but in the present disclosure, the medicinal solution supply unit having the same structure as the conventional medicinal solution supply unit is installed on each side of opposite sides of the left and right. In other words, a pair of the medicinal solution supply units, 3A and 3B, are installed.

In addition, one side of each of the transfer lines L is mounted on a corresponding one of supply nozzles n of each of the medicinal solution supply units 3A and 3B, an opposite side of each of the transfer lines L is mounted in a corresponding one of injection holes h1 of the distribution plate. Accordingly, the medicinal solution stored in the medicinal solution supply units is supplied to the injection holes h1 of the distribution plate through the transfer lines L and is injected into the cavity of the manufacturing roll through the discharge holes h2 of the wedge in communication with the injection holes in a capsule manufacturing process.

Next, the number of injection holes h1 and discharge holes h2 formed in the distribution plate and wedge, respectively, is different compared to that of the existing manufacturing device.

The number of the injection holes h1 of the distribution plate is determined corresponding to the number of the medicinal solution supply nozzles n provided in each of the medicinal solution supply units.

That is, when one medicinal solution supply unit is installed in a center of the existing manufacturing device, the medicinal solution is supplied to the distribution plate from the left and right of the medicinal solution supply unit through the medicinal solution supply nozzles formed on the opposite sides of the left and right of the medicinal solution supply unit, and the injection holes of the distribution plate are also in a shape arranged in a number of one row on each of the left and right of the distribution plate, wherein the number of one row on the distribution plate is the same number of the medicinal solution supply nozzles on each side of the medicinal solution supply unit.

However, in the present disclosure, since two medicinal solution supply units are installed and the medicinal solution is supplied to the distribution plate through the medicinal solution supply nozzles n formed on each of the left and right of each of the medicinal solution supply units, the injection holes h1 in the distribution plate P of the present disclosure take a shape arranged in a number of two rows on each of the left and right of the distribution plate P.

To this end, the distribution plate P of the present disclosure may have a width greater than that of the existing distribution plate.

In addition, the medicinal solution supplied through the injection holes h1 of the distribution plate moves to the wedge W located under the distribution plate and is discharged through the discharge holes h2 formed at the bottom of the wedge, and the number of discharge holes is also determined according to the number of the medicinal solution supply nozzles of the medicinal solution supply units.

That is, a discharge hole h2*a* in communication with one medicinal solution supply nozzle famed on one side of one medicinal solution supply unit 3A and a discharge hole h2*b* in communication with one medicinal solution supply nozzle formed on one side of another medicinal solution supply unit 3B become one unit and are formed at the bottom of the wedge. In addition, the medicinal solution is input into one capsule in which two discharge holes h2*a* and h2*b*, having become one unit, are manufactured.

For reference, each of the transfer lines L connected to one of the medicinal solution supply nozzles n foiled on one side of one medicinal solution supply unit 3A is connected to a corresponding injection hole h1*a* of an inner side line of the injection holes arranged in one of the number of two rows on a relevant one of the left and right of the distribution plate P, and each of the transfer lines L connected to one of the medicinal solution supply nozzles n formed on one side of one medicinal solution supply unit 3B is connected to a corresponding injection hole h1*b* of an outer side line of the injection holes arranged in one of the number of two rows on the relevant one of the left and right of the distribution plate P.

Accordingly, when different types of medicinal solutions are each filled in the medicinal solution supply units 3A and 3B, the medicinal solutions discharged from the two adjacent discharge holes h2*a* and h2*b*, which have become one unit, are different from each other, so that one capsule may be charged with the medicinal solutions different from each other.

According to the manufacturing device of the present disclosure configured as described above, a pair of medicinal solution supply units 3A and 3B, which are structured independently and do not interfere with each other, are provided, so the types of the medicinal solutions being filled into the capsule are not restricted.

For example, when it is necessary to inject two medicinal solutions such as oil and water, which have characteristics incapable of being mixed, into the capsule, it is not possible to fill the two medicinal solutions into the capsule due to the characteristics thereof of not being capable of being mixed even when the two medicinal solutions are stored in a single medicinal solution supply unit as in the existing case and supplied to the capsule manufacturing unit. However, as in the present disclosure, each of the medicinal solutions is stored in each of the medicinal solution supply units, thereby being allowed to be filled into one capsule through each injection hole and discharge hole through a separate transfer line.

Alternatively, when each of the medicinal solutions in liquid and granular states, respectively, should be filled into the one same capsule, the medicinal solutions should be stored and mixed in one medicinal solution supply unit and be filled into the capsule through the same supply line. However, in this case, there is a limitation in that it is difficult to meet a mixing ratio and the like of the medicinal solutions in liquid and granule states required in the capsule. However, according to the manufacturing device of the present disclosure, the two medicinal solutions such as above may be filled in the capsule more easily and precisely than according to the existing one.

That is, according to the device of the present disclosure, the medicinal solutions are injected without interfering with each other in the respective medicinal solution supply unit, and an amount of each of the medicinal solutions supplied from each of the medicinal solution supply units may be controlled.

Alternatively, when one medicinal solution needs to be injected under a vacuum state and another medicinal solution needs to be injected under a state other than the vacuum state, the capsule may be easily charged with both the medicinal solutions by the device of the present disclosure.

Figure 3:
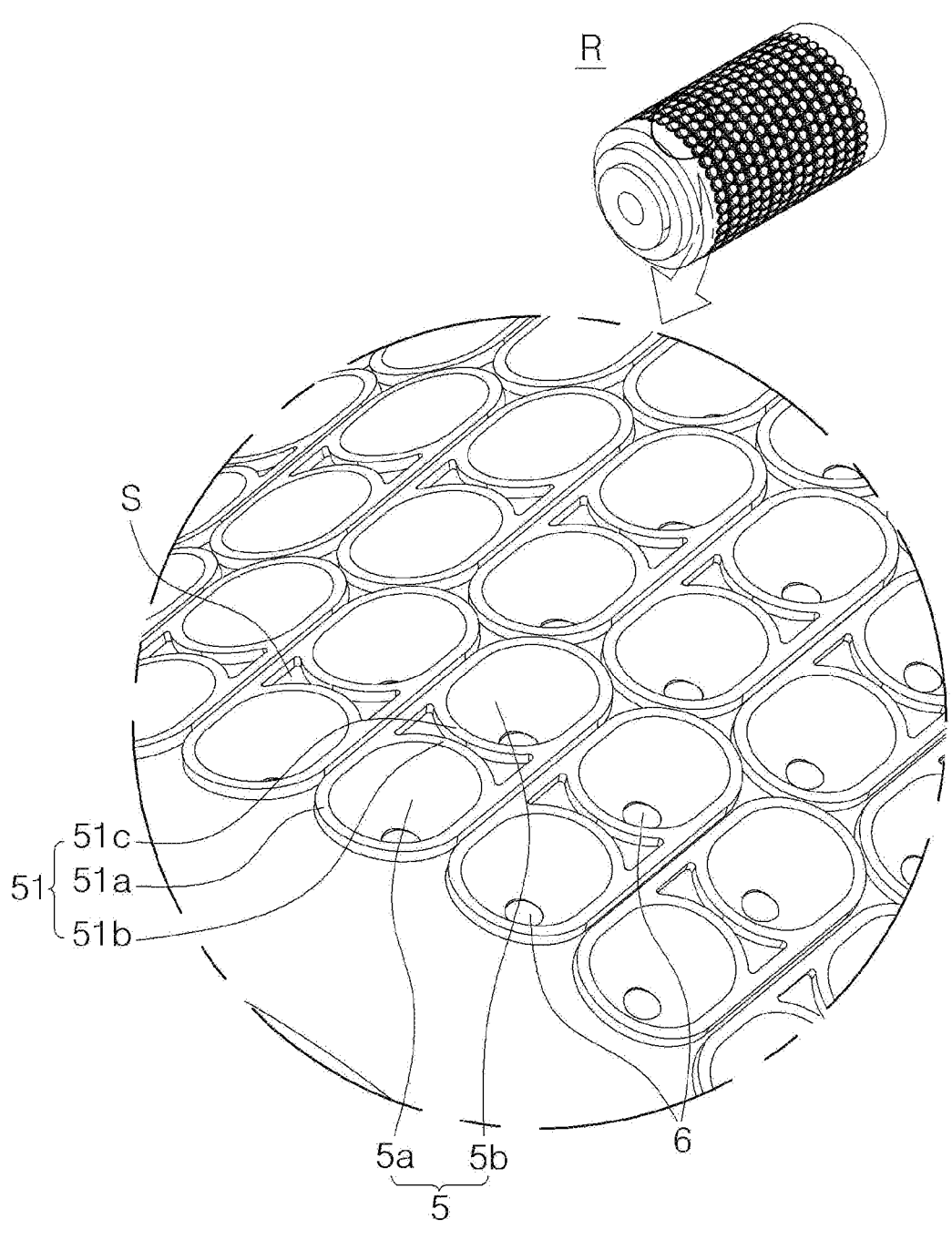
FIG. 3 is a view showing a shape of a manufacturing roll in the manufacturing device for the gelatin capsule according to the present disclosure.

Next, in order that the two medicinal solutions injected into the capsule are not mixed and stored in the capsule, a cavity formed on the surface of the manufacturing roll is structured in a shape as shown in FIG. 3.

That is, as shown in FIG. 3, the cavity 5 engraved on the manufacturing roll in one half of the capsule shape is configured such that the inner space thereof is divided into a first space 5*a* and a second space 5*b*, which are each provided with respective suction holes for suction. In addition, the discharge holes h2*a* and h2*b* formed in the wedge correspond to the first and second spaces, respectively.

In addition, the corresponding cavity 5 is also formed with a pressing part 51 that slightly protrudes from the surface of the manufacturing roll at an edge of the cavity like the existing cavity, wherein the pressing part 51 presses a sheet located between the manufacturing roll and the manufacturing roll together with the pressing part formed at the cavity of the opposite manufacturing roll, thereby causing the sheet to be sealed and laminated.

At this time, as shown in FIG. 3, the pressing part 51 according to the present disclosure includes an outer side pressing part 51a surrounding the edge of the cavity 5, a first inner side pressing part 51b positioned close to the first space, and a second inner pressing part 51c positioned close to the second space, wherein the first inner side pressing part 51b and the second inner pressing part 51c are famed between the first space 5a and the second space 5b, which are divided at the inside of the cavity. In this case, in order to manufacture one capsule whose inner side is divided into two spaces, one space S, which may allow the surface of the manufacturing roll to be exposed, is famed between the first and second inner pressing parts 51b and 51c. Naturally, in this case, the outer side pressing part 51a continuously surrounds the entire edge of the cavity 5.

On the other hand, when the same kind of medicinal solution is filled in the pair of the medicinal solutions supply units 3, it is possible to manufacture a larger number of soft capsules than the conventional manufacturing device for the soft capsule.

In particular, in this case, for the outer side pressing portion 51a formed continuously to surround the edge of the cavity 5 in FIG. 3, when portions of the outer pressing part 51a adjacent to the space S, which allows the surface of the manufacturing roll to be exposed, are cut off, twice as many soft capsules may be manufactured as the existing one with a single injection of a medicinal solution, thus the productivity may be doubly increased.

Alternatively, the manufacturing roll shown in FIG. 3 may be used as it is, but after completion of the capsule, portions of the capsule corresponding to the portions of the outer side pressing part 51a may be cut to finally obtain two capsules from one manufactured product.

In describing the present disclosure above, the present disclosure has been described with reference to the accompanying drawings. However, the present disclosure may be variously modified, changed, and substituted by those skilled in the art and should be interpreted that such modifications, changes, and substitutions belong to the protection scope of the present disclosure.

What is claimed is:

1. A manufacturing device for a gelatin capsule, the device comprising:

a sheet manufacturing unit configured to manufacture a thin film-shaped sheet;

a capsule manufacturing unit comprising a pair of manufacturing rolls configured to manufacture a capsule with the sheet manufactured by the sheet manufacturing unit; and medicinal solution supply units configured to supply a medicinal solution to an inside of the sheet being turned into a capsule, wherein the medicinal solution supply units are installed in a pair, and wherein the medicinal solution supplied from one medicinal solution supply unit and the medicinal solution supplied from the other medicinal solution supply unit are either the same or different from each other, wherein a cavity formed on a surface of each of the manufacturing rolls of the capsule manufacturing unit is configured such that an inner space thereof is divided into a first space and a second space, wherein the medicinal solution discharged from one medicinal solution supply unit of the pair of medicinal solution supply units is injected into the first space, and the medicinal solution discharged from the other medicinal solution supply unit is injected into the second space, wherein the capsule manufacturing unit comprises:

a wedge configured to inject the medicinal solution supplied thereto into the capsule, and a distribution plate installed on a top portion of the wedge and configured to receive the medicinal solution from the pair of medicinal solution supply units, wherein the distribution plate is formed with injection holes through which the medicinal solution is supplied to the wedge, the injection holes being arranged in two rows on each of the left and right sides of the distribution plate, wherein the number of the injection holes arranged in two rows on each of the left and right sides of the distribution plate is the same as that of medicinal solution supply nozzles formed on one side of each of the pair of medicinal solution supply units, and the wedge is formed with discharge holes each of which is in communication with a corresponding injection hole and configured to inject the medicinal solution into the capsule being formed in a capsule manufacturing process, wherein a discharge hole in communication with a medicinal solution supply nozzle formed on one side of one medicinal solution supply unit and a discharge hole in communication with a medicinal solution supply nozzle formed on one side of the other medicinal solution supply unit, as a unit, are arranged corresponding to the first space and the second space, respectively, of the cavity.

2. The device of claim 1, wherein the cavity is formed with a pressing unit protruding from the surface of each of the pair of manufacturing rolls, wherein the pressing unit comprises an outer side pressing part continuously surrounding an edge of the cavity, and a first inner side pressing part and a second inner pressing part formed between the first space and the second space, and wherein a spece exists between the first inner pressing part and the second inner pressing part, optionally the space existing between the first inner pressing part and the second inner pressing part allowing the surface of the manufacturing roll to be exposed.

\* \* \* \* \*